United States Patent
Van Den Eerenbeemd et al.

(10) Patent No.: US 9,268,121 B2
(45) Date of Patent: Feb. 23, 2016

(54) SENSOR DEVICE WITH DOUBLE TELECENTRIC OPTICAL SYSTEM

(75) Inventors: Jacobus Maria Antonius Van Den Eerenbeemd, Nuenen (NL); Jacobus Hermanus Maria Neijzen, Heeze (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 13/990,251

(22) PCT Filed: Nov. 28, 2011

(86) PCT No.: PCT/IB2011/055330
§ 371 (c)(1),
(2), (4) Date: May 29, 2013

(87) PCT Pub. No.: WO2012/073178
PCT Pub. Date: Jun. 7, 2012

(65) Prior Publication Data
US 2013/0248690 A1    Sep. 26, 2013

(30) Foreign Application Priority Data
Dec. 1, 2010 (EP) .................................. 10193351

(51) Int. Cl.
H01L 27/00 (2006.01)
G02B 17/00 (2006.01)
G01N 21/552 (2014.01)
G02B 13/22 (2006.01)
G02B 13/26 (2006.01)
H01L 27/146 (2006.01)

(52) U.S. Cl.
CPC .............. *G02B 17/00* (2013.01); *G01N 21/552* (2013.01); *G02B 13/22* (2013.01); *G02B 13/26* (2013.01); *G02B 17/008* (2013.01); *H01L 27/14625* (2013.01)

(58) Field of Classification Search
CPC ............................... G02B 13/22; G02B 17/008
USPC ....................................................... 250/208.1
See application file for complete search history.

(56) References Cited

U.S. PATENT DOCUMENTS

| | | | | |
|---|---|---|---|---|
| 3,748,015 | A | * | 7/1973 | Offner ........................ 359/366 |
| 5,221,975 | A | * | 6/1993 | Kessler ....................... 358/474 |
| 5,369,521 | A | * | 11/1994 | Yoshino ..................... 359/196.1 |
| 5,548,394 | A | | 8/1996 | Giles |
| 5,708,532 | A | | 1/1998 | Wartmann |
| 5,715,050 | A | | 2/1998 | Haga |
| 6,643,390 | B1 | | 11/2003 | Clark |
| 6,778,267 | B2 | | 8/2004 | Drake |
| 6,980,249 | B2 | | 12/2005 | Albertelli |
| 2001/0001573 | A1 | | 5/2001 | Haga |

(Continued)

FOREIGN PATENT DOCUMENTS

| | | |
|---|---|---|
| CN | 101216597 A | 7/2008 |
| FR | 2582415 A1 | 11/1986 |

(Continued)

*Primary Examiner* — Thanh Luu

(57) ABSTRACT

A sensor device and a method for a double telecentric optical system includes a single focusing element, such as a lens. The device and method further include a mirror element arranged at a focal point of the single focusing element to reflect incoming light rays back to the single focusing element. The incoming and reflected light rays pass through different parts of the single focusing element to allow for a spatially separated arrangement of an object and its image.

14 Claims, 4 Drawing Sheets

(56) References Cited

U.S. PATENT DOCUMENTS

2004/0130723 A1 7/2004 Yager et al.
2009/0262323 A1* 10/2009 Sasaki .............................. 355/68

FOREIGN PATENT DOCUMENTS

| | | |
|---|---|---|
| JP | 6109443 A | 4/1994 |
| JP | 06118341 A | 4/1994 |
| JP | 2006288526 A | 10/2006 |
| WO | 0208139 A2 | 1/2002 |
| WO | 2005113832 A2 | 12/2005 |
| WO | 2007050743 A2 | 5/2007 |
| WO | 2009112905 A2 | 9/2009 |
| WO | 2010064170 A1 | 6/2010 |

* cited by examiner

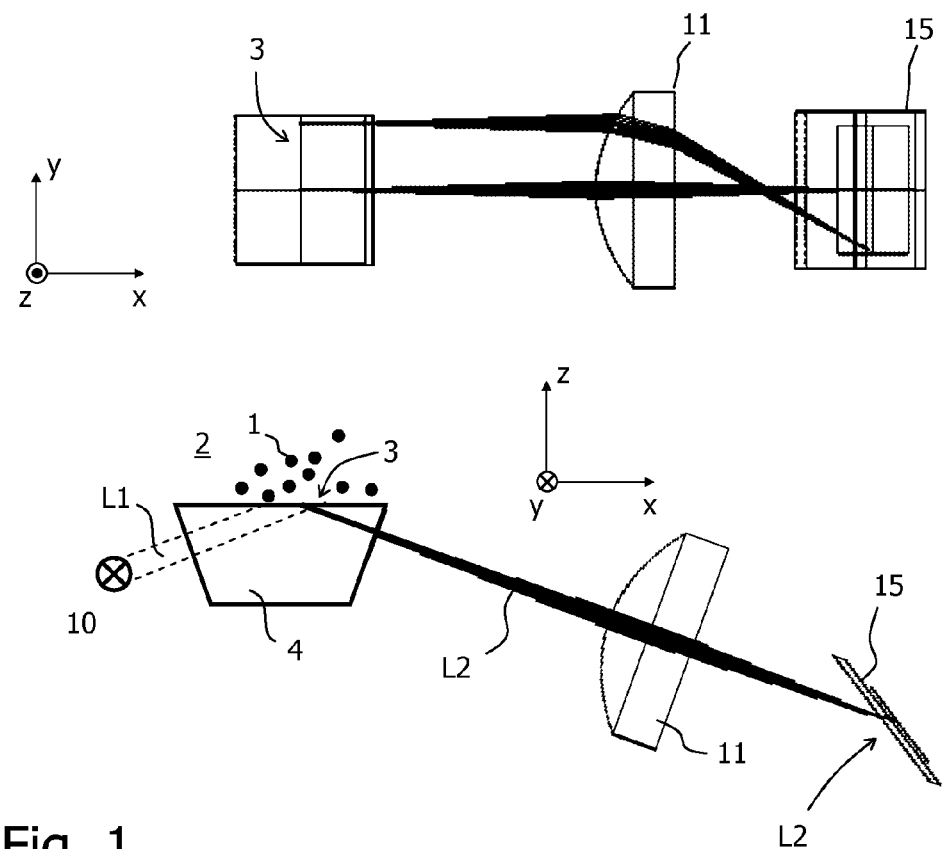
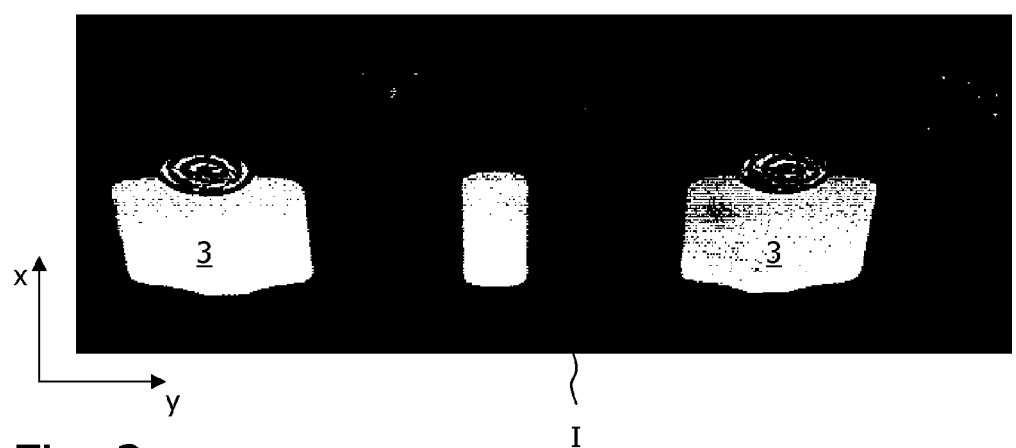
Fig. 1
Fig. 2

SENSOR DEVICE WITH DOUBLE TELECENTRIC OPTICAL SYSTEM

FIELD OF THE INVENTION

The invention relates to a double telecentric optical system, to a method for generating an image of an object, and to a sensor device comprising a double telecentric optical system.

BACKGROUND OF THE INVENTION

The WO 2009/112905 A2 discloses an optical biosensor in which an input light beam is totally internally reflected at a contact surface and the resulting output light beam is detected by a camera and evaluated with respect to the amount of target components at the contact surface. The target components comprise magnetic particles as labels, which allows to affect the processes in the sample by magnetic forces. In this and similar optical sensor devices, the imaged object plane is tilted with respect to the optical axis of the camera, which makes it difficult to evaluate its image.

SUMMARY OF THE INVENTION

Based on this background it was an object of the present invention to provide means that allow for an improved imaging of an object onto an image sensor, particularly if said object is tilted with respect to an optical axis.

This objective is achieved by a double telecentric optical system according to claim 1, a method according to claim 2, and sensor devices according to claims 3 and 13. Preferred embodiments are disclosed in the dependent claims.

According to its first aspect, the invention relates to a double telecentric optical system that is intended for generating a (real) image of an object. Double telecentric optical systems are defined by the fact that the entrance pupil and the exit pupil are (virtually) located at infinity. This means that all chief rays are parallel to the optical axis in object and image space. A chief ray goes through the optical axis at the position of the stop. A double telecentric optical system according to the invention comprises the following components:

a) A focusing element that focuses light rays coming from the object to a focal point. Due to the double telecentric design, only light rays that are substantially parallel to the optical axis of the focusing element play a role in this context, wherein the "optical axis" is as usual defined as a line along which there is some rotational symmetry of the focusing element, for example a line that passes through the centers of curvature of optical surfaces of the focusing element.

b) A mirror element that is arranged at said focal point and that reflects light rays, which come from the object and have been focused by the focusing element to the focal point, back to the focusing element. The reflected light rays will hence encounter the focusing element a second time.

According to its second aspect, the invention relates to a method for generating an image of an object, said method comprising the following steps which may be executed in the listed or any other appropriate order:

a) Focusing with a focusing element light rays coming from the object to a focal point.

b) Reflecting with a mirror element said focused light rays back to the focusing element.

According to its third aspect, the invention relates to a sensor device for the examination of a sample, said sensor device comprising the following components:

a) A sensing region at which a sample can be provided.

b) An image sensor, for example a CCD or CMOS chip of a camera.

c) A double telecentric optical system that is arranged to image said sensing region (as an object) onto said image sensor and that comprises a focusing element for focusing light rays coming from the object to a focal point and a mirror element arranged at said focal point for reflecting said focused light rays back to the focusing element. The double telecentric optical system may hence particularly be designed according to the first aspect of the invention.

The double telecentric optical system, the method, and the sensor device according to the invention are related by the features of the optical system. Definitions, explanations, or modifications explained with respect to one of these elements will therefore analogously be valid for the other elements, too.

The double telecentric optical system, the method, and the sensor device have the common feature that they comprise a single focusing element by which light rays coming from an object as well as light rays that generate an image of the object are affected. This allows for a very compact design in comparison to known double telecentric optical systems, in which two focusing elements are needed and arranged such that their focal points coincide.

In the following, various preferred embodiments of the invention will be described that relate to the optical system, the method, and the sensor device defined above.

According to a first preferred embodiment, the design of the double telecentric optical system is such that, on the one hand side, light rays coming from the object and, on the other hand side, light rays reflected by the mirror element encounter different parts of the focusing element. In this way it is possible to spatially separate the object from its image in a compact arrangement.

In a further development of the aforementioned embodiment, said different parts of the focusing element are arranged symmetrically with respect to the optical axis of the focusing element. The optical axis may particularly be located in a plane that divides space into two half-spaces, wherein each half-space comprises another one of the two different parts of the focusing element and wherein one half-space comprises the object and the other half-space comprises its image.

The mirror element of the optical system is preferably designed as a stop, or it comprises a stop. The stop of a double telecentric optical system determines the width of the light bundles that can enter and leave said system. As the mirror element is arranged at the focal point of the focusing element, it can advantageously fulfill the function of such a stop or be combined with such a stop.

In general, the focusing element is by definition an optical component that can focus incoming parallel light rays to a focal point. One particular embodiment of such a focusing element is a lens, particularly a converging lens. Another possible embodiment of the focusing element is a mirror, particularly a concave (e.g. spherical, parabolic etc.) mirror.

According to another embodiment of the invention, the plane of the object and/or the image is tilted with respect to the optical axis of the focusing element. This allows to use the available limited space more economically.

In another embodiment of the invention, an additional mirror may be disposed between the focusing element and the generated image in the optical path of the light rays that have been reflected by the mirror element. This increases the freedom with respect to the position where the image is generated or captured.

The sensor device may particularly comprise a light source for illuminating the sensing region. The resulting reflected, scattered, or otherwise generated light can then be processed by the optical system to generate an image of the sensing region.

According to a further development of the aforementioned embodiment, the light source of the sensor device is arranged in such a way that it can illuminate the sensing region by total internal reflection. To this end, light rays from the light source must hit the sensing region under an angle larger than the critical angle of total internal reflection, wherein the illumination is achieved by evanescent waves generating during this process. This design allows to apply frustrated total internal reflection (FTIR) for the detection of target components in the sensing region.

According to a fourth aspect, the invention relates to a sensor device comprising the following components:

a) A sensing region at which a sample can be provided.
b) A light source that is arranged to illuminate the sensing region by total internal reflection.
c) An image sensor.
d) A double telecentric optical system that is arranged to image the sensing region onto the image sensor.

The described sensor device uses frustrated total internal reflection (FTIR) in combination with a double telecentric optical system. Definitions, features, and modifications explained above with respect to these elements will therefore analogously apply to this FTIR sensor device, which has the advantage that the sensing region can be imaged onto the image sensor without optical distortions like a keystone effect.

According to a further development of the aforementioned embodiment, the FTIR sensor device comprises two focusing elements and at least one mirror arranged in the optical path between them. By using at least one mirror, a compact design of the sensor device can be achieved. The focusing elements may particularly be lenses. Moreover, it is preferred that two (or more) mirrors are used to fold the light path, yielding a particularly compact design.

The invention further relates to the use of the sensor devices described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which:

FIG. 1 schematically shows a top view (top) and a side view (bottom) of a sensor device with a single lens for imaging sensing regions;

FIG. 2 shows an image of the sensing regions obtained with a sensor device according to FIG. 1;

Like reference numbers or numbers differing by integer multiples of 100 refer in the Figures to identical or similar components.

DESCRIPTION OF PREFERRED EMBODIMENTS

Figure 3:
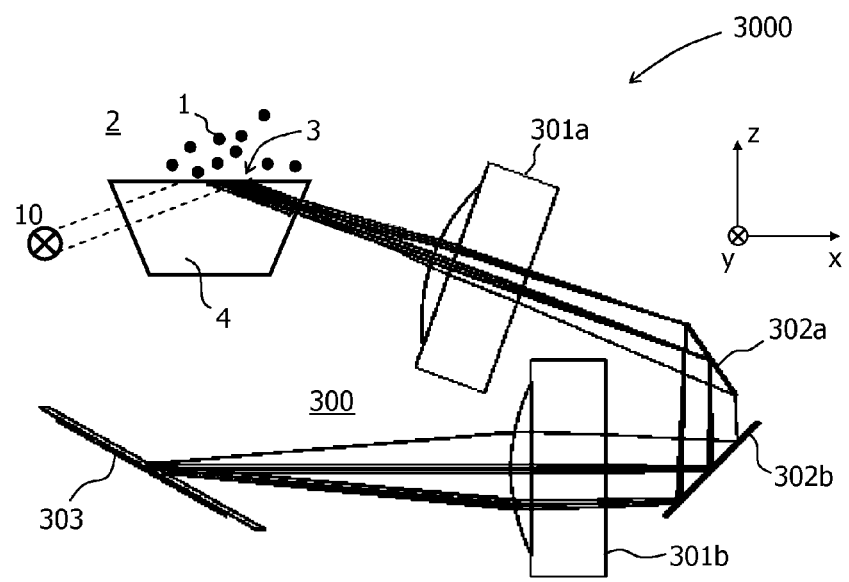
FIG. 3 schematically shows a side view of a sensor device with two lenses in a double telecentric arrangement for imaging sensing regions.

The invention will in the following be explained with respect to biosensors for the detection of specific components in samples like body fluids (e.g. saliva, urine, or blood), though the invention is not limited to such applications. FIG. 1 schematically shows essential components of an optical biosensor in a top view and a side view. The biosensor makes use of magnetic particles 1 (beads) that are covered with antibodies and provided in a sample chamber 2, for example of a disposable cartridge 4 (only its bottom side is schematically indicated). Moreover, it may comprise magnets (not shown) for the execution of specific magnetic actuation protocols to optimize the assay performance.

The presence of target molecules in a sample is detected with such a biosensor by the binding or prohibited binding of magnetic beads 1 to sensing regions 3 (detection spots) that are covered with specific antibodies. The presence of beads bound to a sensing region 3 is detected by optical means, for example by frustrated total internal reflection (FTIR). To this end, the surface of the cartridge containing the sensing regions 3 is imaged by a lens 11 on an image sensor 15, for example a CCD camera or CMOS detector. An illumination beam L1 that is provided by a light source 10 approaches the area of interest under an angle larger than the critical angle for total internal reflection. The reflected light beam L2 is imaged on the detector 15. The evanescent field at the position of the sensing regions 3 in the biosensor can interact with the magnetic beads 1 close to the surface, thereby reducing the intensity of the reflected beam L2. In this way the spots where beads are bound on the cartridge surface become visible as dark spots in the generated image I. Further details of this procedure may be found in the WO 2010/064170 A1, which is incorporated into the present text by reference.

It should be noted that the incident angle of the illumination light beam L1 and the angle of the reflected light beam L2 on the imaging side are equal in the shown embodiments in which FTIR is applied as detection method. This is however not needed for the present invention. If e.g. luminescence would be used it could be beneficial to illuminate at an angle different from the detection angle (the cartridge geometry would then of course be different, too).

According to FIG. 1, a telecentric illumination is used. With this, telecentricity cannot be achieved at the detector 15 with a single lens design. Moreover, the object plane 3 is tilted; hence the detector 15 also needs to be tilted to achieve a sharp image over the entire image field (sometimes referred to as the Scheimpflug criterion, cf. "Optical methods of measurement" by Sirohi and Chau, Dekker 1999). Due to this geometry the magnification changes over the viewing field. This has two effects. One, the image I suffers from keystone distortion. And two, the intensity has a gradient over the viewing field. These two effects are visible in the FTIR-image I of a cartridge shown in FIG. 2.

The aforementioned effects can be eliminated by using a double telecentric design. But this requires two lenses. FIG. 3 shows an FTIR sensor device 3000 comprising a double telecentric optical system 300 with two lenses 301a and 301b in which the lightpath is folded by two mirrors 302a, 302b to fit to the space confinements in a handheld reader.

Figure 4:
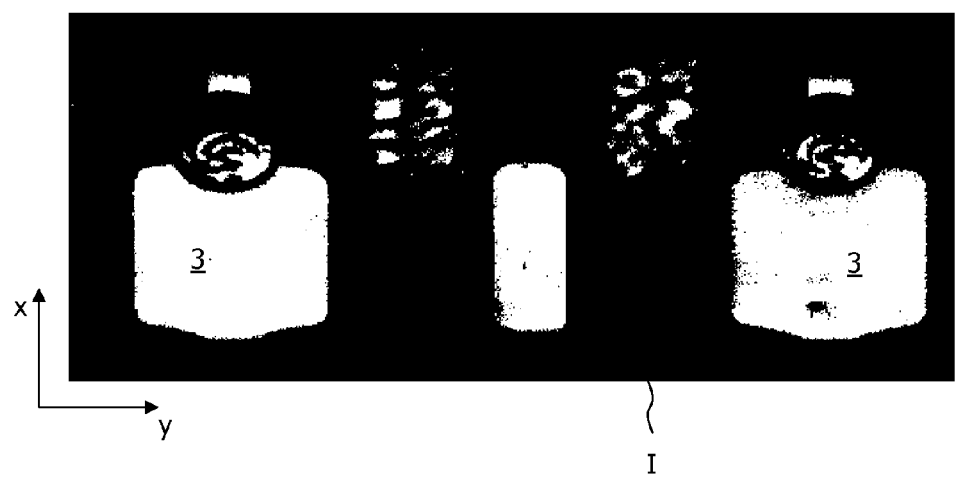
FIG. 4 shows an image of the sensing regions obtained with a sensor device according to FIG. 3.

FIG. 4 shows an FTIR-image I of a cartridge generated with the aforementioned design. It can be seen that keystone distortion and the intensity gradient are absent. This is due to the fact that the magnification M is no longer determined by the object distance but by the ratio of the focal lengths $f_1$, $f_2$ of the used lenses: $M_y=-f_2/f_1$. By using lenses with equal focal lengths, a magnification of −1.0 results. In the x-direction the situation is a bit more complicated due to the fact that the, over the y-axis, tilted object plane is contained in a medium with a different refractive index than that of the medium in image space. If we denote the angle between the object resp. image plane and the optical axis with cc resp. β the following relations hold: $\tan[\beta]=n*\tan[\alpha]$, $M_x=-f_2*\sin[\alpha]/(f_1*\sin[\beta])$, in which n is the ratio between the refractive indices of the media in object and image space.

The two lenses 301a, 301b in the double telecentric design of FIG. 3 actually form a telescope, i.e. the focal points of both lenses coincide. Telecentricity is assured by placing the stop at this position. However, due to the limited space in a handheld biosensor, the two fold mirrors 302a, 302b are needed between the lenses 301a, 301b. This leaves insufficient design freedom to place the stop at the correct position.

It is therefore proposed to build a double telecentric system with a single focusing element and a mirror placed at its focus. By this the mirror automatically becomes the stop. By placing the object 3 at a certain height from the optical axis OA the image I can be separated from the object. This approach is facilitated by the fact that the field height is limited in the described biosensor system (cf. FIG. 1: extension of the sensing region 3 is larger in y-direction than in x-direction). Due to this only a limited part of the lens surface is used. By shifting the object height and going back through the lens, the lens surface is used more efficiently. The magnification equals −1.0 as the same lens is used twice.

Figure 5:
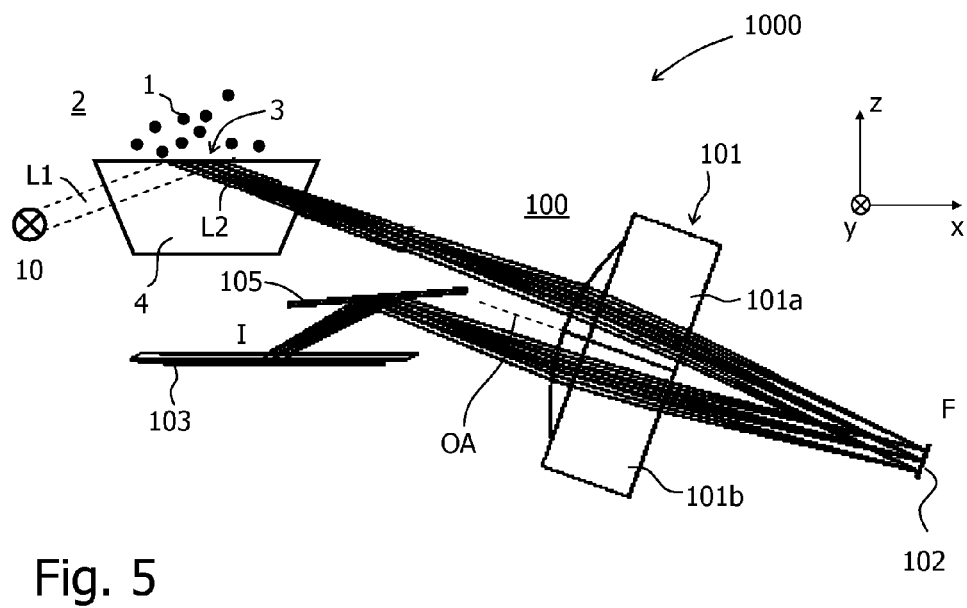
FIG. 5 schematically shows a side view of a sensor device with a double telecentric optical system having a single lens.

FIG. 5 illustrates a sensor device 1000 with a double telecentric optical system 100 according to a concrete embodiment of the aforementioned general principles. As in the previous embodiments, the sensor device 1000 comprises a sample chamber 2 in which a sample with components of interest, for example magnetic particles 1, can be provided. The sample chamber 2 is typically accommodated in a disposable cartridge (not shown) and comprises a surface with at least one sensing region 3 at which target components can bind. An input light beam L1 from a light source 10 is totally internally reflected in the sensing region(s) 3 into an output light beam L2.

A double telecentric optical system 100 is provided to generate an image I of the sensing region 3 (as object) on the plane of an image sensor 103. It comprises a single (convergent) lens 101 and a (planar) mirror element 102 disposed at the focal point F of said lens 101. The lens 101 is arranged such that only its upper half 101a is traversed by the output light beam L2 coming from the object 3. The mirror element 102 is arranged to reflect the incidental light towards the lower half 101b of the lens 101 such that it does not interfere with the incident light. In this way a double telecentric arrangement can be achieved with a single focusing element, i.e. the single lens 101. In practice the stop at the focal point, that is needed in a double telecentric design, will be formed by a hole in a machined housing (not shown) onto which the mirror element 102 is glued.

As shown in FIG. 5, an additional fold mirror 105 may optionally be placed between the lens 101 and the detector 103 with a fold angle that enables a convenient placement of the detector. The orientation of this fold mirror 105 is for example such that the detector 103 can be placed horizontally which may be advantageous from a manufacturing point of view.

Figure 7:
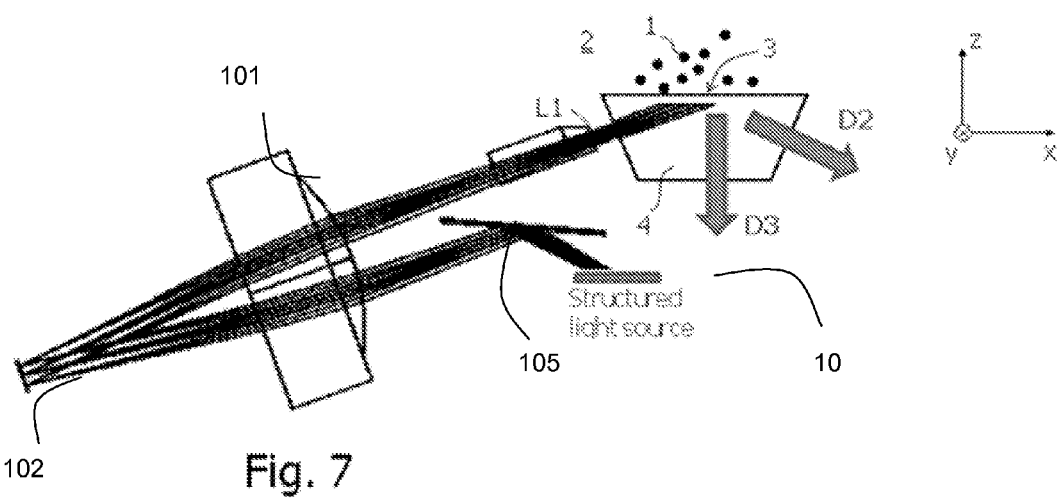
FIG. 7 schematically shows an example of the double telecentric optical system in which the direction of light beams is reversed, the light from the source first passes the lens, and thereafter impinges on the sensing region.

An option regarding FIG. 5 is to change the described configuration in a way to achieve illuminating only specific areas of the cartridge 4, as depicted in FIG. 7. The direction of rays is inverse to the direction described above. The detector 103 in FIG. 5 is in this option of FIG. 7 omitted and replaced by the light source 10 which is correspondingly omitted at the place depicted in FIG. 5. This is depicted in FIG. 7. By using a structured light source 10 (pixilated, like a display) or a light source 10 behind a structured diaphragm, or a light source 10 consisting of a few separate LEDs, only very specific areas of the sensing region or object 3 are illuminated. So, instead of imaging the sensing region 3 on an image sensor 103 as under FIG. 5, a structured light source 10 on the sensing region 3 is imaged in FIG. 7. The arrows denoted with D2 and D3 in FIG. 7 show the direction of the light beams in which direction detectors (not shown) can be implemented behind the optical system to detect the particles 1 at the cartridge 4. The box L1 between the lens 101 and the cartridge 4 is a window through which the beam transmits and has no functionality here.

Figure 6:
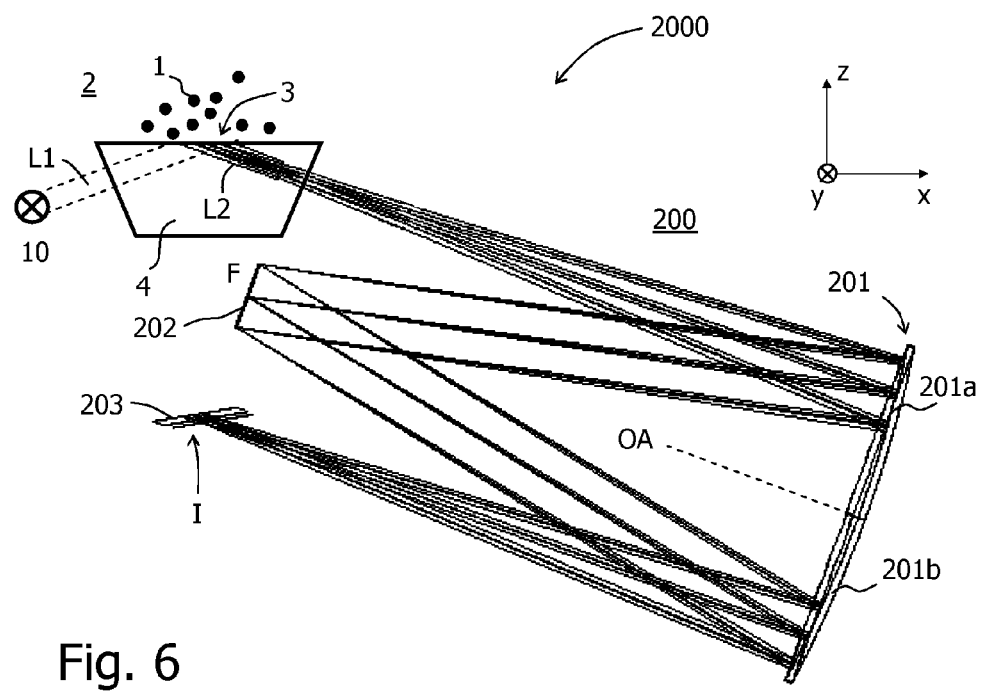
FIG. 6 schematically shows a side view of a sensor device with a double telecentric optical system having a single parabolic mirror.

FIG. 6 shows an alternative solution in which a single spherical or parabolic mirror 201 is used as focusing element (instead of the lens 101 of FIG. 5). Moreover, there is no additional fold mirror in front of the detector 203. Besides this, the design and function of the double telecentric optical system 200 is equivalent to that of FIG. 5 and therefore needs not be described again.

In summary, the invention relates to a double telecentric optical system 100, 200 and its use in a sensor device 1000, 2000, wherein said optical system comprises a single focusing element, for example a lens 101 or a mirror 201. A mirror element 102, 202 arranged at the focal point F of this focusing element reflects incoming light rays back to the focusing element. Incoming and reflected light rays preferably encounter different parts of the focusing element, allowing a spatially separated arrangement of object 3 and its image I.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for generating an image of an object, said method comprising acts of:
illuminating an object provided at a sensing region with a light source;
focusing with a single focusing element light rays coming from the object to a focal point, said light rays coming from the object to the focal point being focused light rays; and
reflecting with a mirror the focused light rays back to the single focusing element, said focused light rays back to the single focusing element being reflected light rays, wherein a plane of at least one of the object and of the image is tilted with respect to an optical axis of the single focusing element,
wherein the single focusing element consists of one of a single lens and a single concave mirror,
wherein the light source is configured to illuminate the sensing region by total internal reflection, and wherein light rays emitted from the light source contact the sensing region at an incident angle of illumination that is larger than a critical angel of the total internal reflection.

2. The method according to claim 1, wherein the focused light rays coming from the object and reflected light rays reflected by the mirror element encounter different parts of the single focusing element.

3. The method according to claim 2, wherein said different parts are arranged symmetrically with respect to the optical axis of the single focusing element.

4. The method according to claim 1, wherein the mirror element comprises a stop.

5. A sensor device, comprising:
a sensing region at which a sample can be provided;
an image sensor;
a double telecentric optical system configured to image the sensing region onto the image sensor, the double telecentric optical system comprising:
a single focusing element for focusing light rays coming from the sensing region to a focal point, said focusing light rays being focused light rays, and
a mirror element arranged at said focal point for reflecting the focused light rays back to the single focusing element, said focused light rays reflecting back being reflected light rays; and
a light source for illuminating the sensing region wherein a plane of at least one of an object and of an image is tilted with respect to an optical axis of the single focusing element,
wherein the single focusing element consists of one of a single lens and a single concave mirror,
wherein the light source is configured to illuminate the sensing region by total internal reflection, and
wherein light rays emitted from the light source contact the sensing region at an incident angle of illumination that is larger than a critical angel of the total internal reflection.

6. The sensor device according to claim 5, wherein the single lens of the single focusing element is a converging lens.

7. The sensor device according to claim 5, wherein the single concave mirror of the single focusing element is one of a spherical mirror and a parabolic mirror.

8. The sensor device according to claim 5, further comprising an additional mirror disposed in an optical path of the reflected light rays between the single focusing element and the image sensor.

9. The sensor device according to claim 5, wherein the illuminating of the sensing region is by evanescent waves.

10. The sensor device according to claim 5, wherein an incident angle of illumination at the sensing region and an angle of the reflected light rays at the image sensor are a same angle.

11. A method for at least one of a molecular diagnostics, a biological sample analysis, a chemical sample analysis, food analysis, and a forensic analysis, the method using a sensor device, the method comprising:
illuminating an object provided at a sensing region with a light source;
focusing with a single focusing element light rays coming from the object to a focal point, said light rays coming from the object to the focal point being focused light rays; and
reflecting with a mirror the focused light rays back to the single focusing element, said focused light rays back to the single focusing element being reflected light rays,
wherein a plane of at least one of the object and of the image is tilted with respect to an optical axis of the single focusing element,
wherein the single focusing element consists of one of a single lens and a single concave mirror,
wherein the light source is configured to illuminate the sensing region by total internal reflection, and
wherein light rays emitted from the light source contact the sensing region at an incident angle of illumination that is larger than a critical angel of the total internal reflection.

12. A sensor device, comprising:
a sensing region at which a sample can be provided;
an image sensor;
a double telecentric optical system configured to image the sensing region onto the image sensor, the double telecentric optical system comprising:
a single focusing element for focusing light rays coming from the sensing region to a focal point, said focusing light rays being focused light rays, and
a mirror element arranged at said focal point for reflecting the focused light rays back to the single focusing element, said focused light rays reflecting back being reflected light rays; and
a light source for illuminating the sensing region wherein a plane of at least one of an object and of an image is tilted with respect to an optical axis of the single focusing element,
wherein the single focusing element consists of one of a single lens and a single concave mirror, and
wherein the light source is configured to illuminate the sensing region by frustrated total internal reflection.

13. A method for generating an image of an object, said method comprising acts of:
illuminating an object provided at a sensing region with a light source;
focusing with a single focusing element light rays coming from the object to a focal point, said light rays coming from the object to the focal point being focused light rays; and
reflecting with a mirror the focused light rays back to the single focusing element, said focused light rays back to the single focusing element being reflected light rays,
wherein a plane of at least one of the object and of the image is tilted with respect to an optical axis of the single focusing element,
wherein the single focusing element consists of one of a single lens and a single concave mirror, and
wherein the light source is configured to illuminate the sensing region by frustrated total internal reflection.

14. A method for at least one of a molecular diagnostics, a biological sample analysis, a chemical sample analysis, food analysis, and a forensic analysis, the method using a sensor device, the method comprising:
illuminating an object provided at a sensing region with a light source;
focusing with a single focusing element light rays coming from the object to a focal point, said light rays coming from the object to the focal point being focused light rays; and
reflecting with a mirror the focused light rays back to the single focusing element, said focused light rays back to the single focusing element being reflected light rays,
wherein a plane of at least one of the object and of the image is tilted with respect to an optical axis of the single focusing element,
wherein the single focusing element consists of one of a single lens and a single concave mirror, and
wherein the light source is configured to illuminate the sensing region by frustrated total internal reflection.

* * * * *